US00PP11183P

United States Patent [19]

Izsak et al.

[11] Patent Number: Plant 11,183

[45] Date of Patent: Jan. 18, 2000

[54] STRAWBERRY PLANT NAMED 'YAEL'

[75] Inventors: Eva Izsak; Shamai Izhar, both of Rehovot, Israel

[73] Assignee: State of Israel, Ministry of Agriculture, Agricultural Research Organization, Bet Dagan, Israel

[21] Appl. No.: 08/968,823

[22] Filed: Nov. 14, 1997

[51] Int. Cl.[7] ..... A01H 5/00

[52] U.S. Cl. ..... Plt./208

[58] Field of Search ..... Plt./48, 49, 208, Plt./209

*Primary Examiner*—Howard J. Locker
*Assistant Examiner*—Ashwin Mehta
*Attorney, Agent, or Firm*—Browdy and Neimark

[57] ABSTRACT

A new and distinct variety of strawberry (*Fragaria L.*) called 'Yael' is a cross between 'Oso Grande' and 'Dorit', and flowers early to medium on a scale of "very early" to "very late".

2 Drawing Sheets

FIELD OF THE INVENTION

The present invention relates to a new and distinct variety of strawberry (*Fragaria L.*) called 'Yael'.

BACKGROUND

This new variety was developed from an organized scientifically designated breeding program, carried out at the Agricultural Research Organization, the Volcani Center, Bet Dagan, Israel. This new variety originated as a single seedling selected from a seedling population obtained from crosses between the strawberry varieties 'Oso Grande' and 'Dorit'. The variety was asexually vegetatively propagated at Bet Dagan, Israel, through runners and the propagation ran true.

SUMMARY OF THE INVENTION

The new variety 'Yael' is able to grow in September and produce fruit starting in November and lasting until summer. The production of fruit beginning in NOvember (Northern Hemisphere, latitude 30–33 degrees) is two months earlier than short day varieties of *Fragaria L.* The fruit of the 'Yael' variety is characterized by good taste, good shape and good size.

DETAILED BOTANICAL DESCRIPTION OF THE INVENTION

Figure 1:
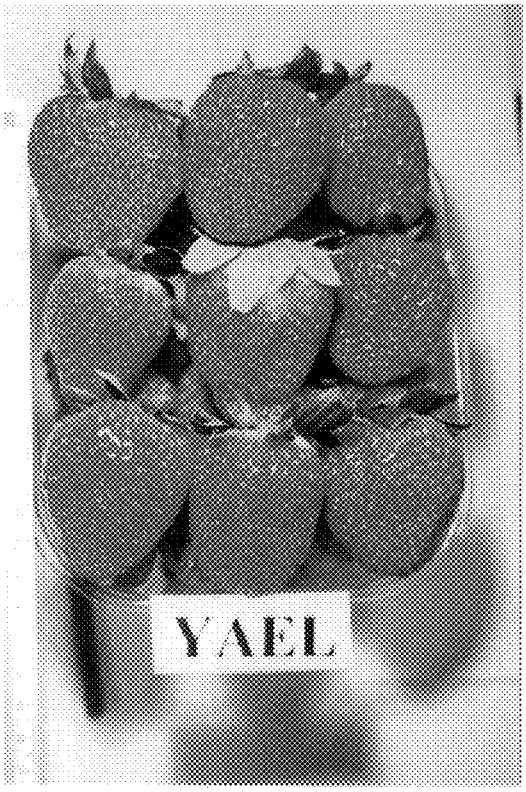
FIG. 1: Photograph of the 'Yael' variety, illustrating the fruits.
Figure 2:
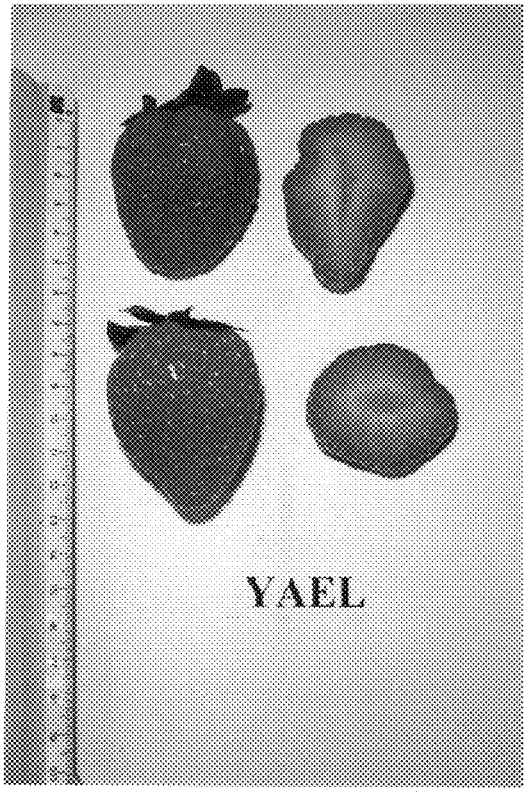
FIG. 2: Photograph of the 'Yael' variety, illustrating a cross-section of the fruits.
Figure 3:
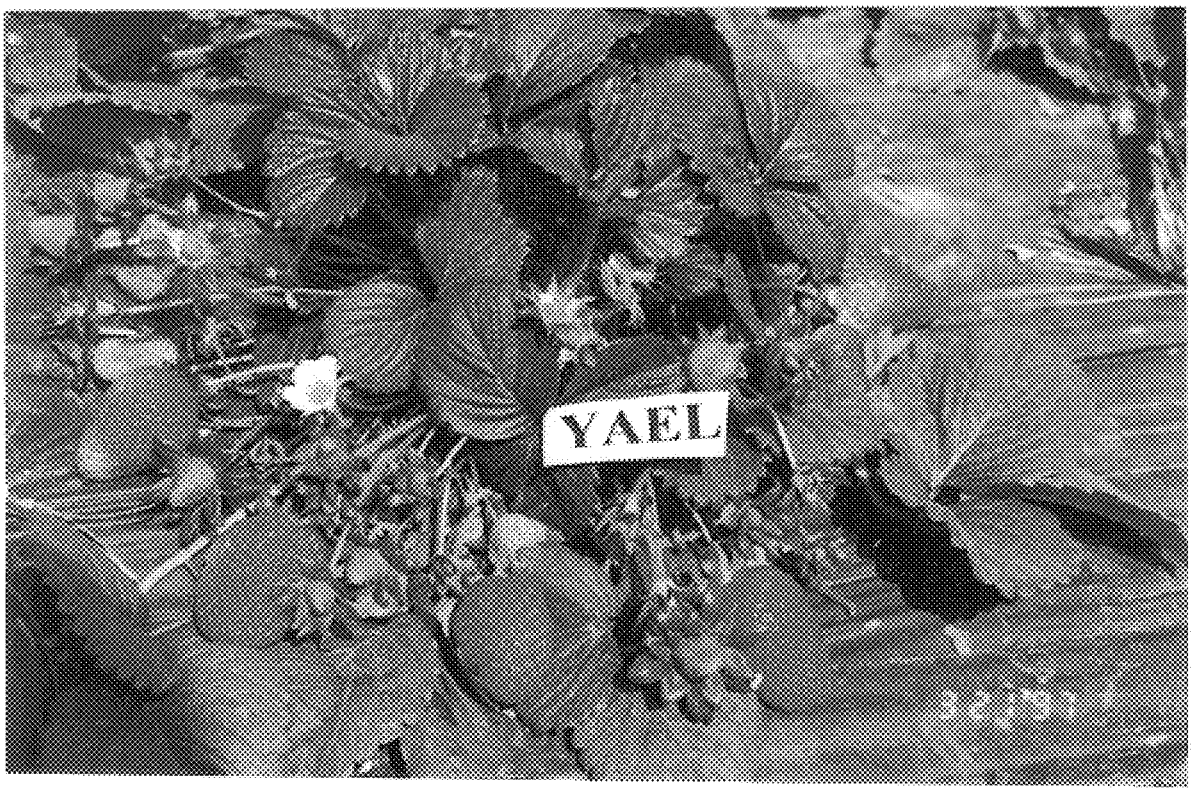
FIG. 3: Photograph of the 'Yael' variety, illustrating the entire plant with foliage, flowers and fruit.

The "Yael" variety was grown in winter, under polyethylene tunnels in Israel. 'Yael' is an infra short day variety, which flowers earlier than short day type strawberry varieties. Infra-Short-Day (I.S.D.) varieties are defined as varieties that initiate flower bud primordia under long light regimes of 13–14 hours at the time night temperatures are about 22° C., compared to strawberry varieties classified as short-day or day-neutral, that do not initiate flower bud primordia under above-mentioned conditions, thus resulting in early flowering and fruit production. The plants are grown in polyethylene tunnels to prevent malformation of the fruit that can be caused by wind and rain. Flowering and fruit production are not affected by the use of polyethylene tunnels.

This production procedure is utilized in normal agricultural practices by the skilled artisan and does not involve temperature or light control. Plants were stored at 0° C. from January through April. They were then planted in the nursery without further treatment. Runners with plantlets were produced during summer. These young plantlets were collected from the nursery in September and transferred to raised beds. Average temperatures at that time of the year are 30° C. during the day and 22° C. at night. Water and fertilizers were applied through drip irrigation.

An example of an optimum planting date is between September 5 and 15, with the approximate date of flowering on October 1–15, and the approximate date of first fruiting on November 5–15. If planting is September 25–30, the approximate date of fruit flowering is October 25–30, and first fruiting is approximately November 25–30. Flowering is not induced by chilling, but by natural exposure to short day length (long nights) characteristic of late fall and early winter.

Strawberry plants in general are self-fertile, as is 'Yael'; no pollinator is needed as pollination is brought about by insects and wind.

Color readings described herein were taken under natural light conditions and color identifications were made by reference to The Royal Horticultural Society Colour Chart (R.H.S.C.C.) except where common terms of color definition are employed.

The pertinent characteristics of the present invention are presented in Table 1 and Table 2.

Additionally, the variety 'Yael' (1) has no tendency toward fruit malformation; (2) disease resistance appears normal in that no particular problematic conditions arose during trials; and (3) the type of bearing is not remontant, i.e. "Yael" blooms continuously during late fall and winter.

Fruit shape of 'Yael' is similar to the strawberry variety 'Dorit' (U.S. Plant Pat. No. 7,869). The fruit is longer than broad, with primary, secondary and tertiary fruit possessing almost similar shape (Table 2). The fruit is of medium firmness with a red color (Table 2).

The variety 'Yael' flowers two months earlier than known short-day strawberry varieties. A close known variety would be 'Dorit' U.S. Plant Pat. No. 7,869 (Table 1); also see the new varieties mentioned in: U.S. Plant Pat. No. 7,881

('Sharon'); U.S. Plant Pat. No. 7,876 ('Shalom'); U.S. Plant Pat. No. 7,865 ('Smadar'); U.S. Plant Pat. No. 8,746 ('Ofra'); U.S. Plant Pat. No. 8,748 ('Virginia'); U.S. Plant Pat. No. 8,747 ('Nama').

Additionally, early flowering results in early fruit production. Total Soluble Solids (T.S.S), percent acidity, aroma evaluation and taste are presented in Table 4, by comparing to the varieties listed in Table 3.

TABLE 1

PLANT CHARACTERISTICS OF YAEL

| MORPHOLOGICAL TRAIT<br>Botanical Classification | DESCRIPTION<br>*Fragaria L.* |
|---|---|
| Plant | |
| 1) Height | 17–21 cm |
| 2) Diameter | 31–35 cm |
| 3) Habit | Globose |
| 4) Density | Dense |
| 5) Vigor | Strong |
| Leaf: | |
| 1) Length | 21–24 cm |
| 2) Width | 16–19 cm |
| 3) Green Color of Upper Side | Medium RHS ca. 147 AB |
| 4) Blistering | Medium |
| 5) Cross section | Concave |
| 6) No. of leaflets | Sometimes > 3 |
| Petiole | |
| 1) Length | 9–12 cm |
| 2) Thickness | 4–6 mm |
| 3) Pubescence | Strong |
| 4) Green Color | Light RHS ca. 144 C |
| Terminal leaflet | |
| 1) Length/Width ratio | Longer than broad |
| 2) Shape of base | Obtuse |
| 3) Shape of Teeth | Rounded |
| 4) Length | 7–8 cm |
| 5) Width | 7–8 cm |
| Calyx | |
| 1) Diameter of Primary Calyx | 40–50 mm |
| 2) Diameter of Secondary Calyx | 28–38 mm |
| 3) Diameter of Tertiary Calyx | 32–35 mm |
| 4) Size of Inner Calyx in relation to Out Calyx | Same size |
| Flower | |
| 1) Diameter of Primary Flower | 25–28 mm |
| 2) Diameter of Secondary Flower | 21–26 mm |
| 3) Diameter of Tertiary Flower | 20–26 mm |
| 4) Spacing of petals | Touching |
| 5) Petal length | 11–12 mm |
| 6) Petal width | 10–13 mm |
| 7) Petal length/width | Broader than long |
| 8) TIme of beginning of flowering | Early to medium |
| 9) Fragrance | None |
| Stolon | |
| 1) Number per Plant | ca. 13 |
| 2) Thickness | 3.5–4 mm |
| 3) Pubescence | Weak |
| 4) Anthocyanin coloration | Strong |
| Infloresence | |
| 1) Position relative to foliage | At level with |
| 2) Peduncle length | ca. 10 cm |
| 3) Peduncle thickness | ca. 3 mm |
| 4) Peduncle color | light green RHS ca. 144C |
| 5) Peduncle pubescence | strong |

The description of 'Yael' is based on the test guidelines for *Fragaria L.* of the International Union for the Protection of New Plant Varieties (UPOV). Only characteristics which are relevant for comparing varieties are listed; for example, there are no varietal differences acknowledged in the characteristic "color of lower side of leaf".

The time of beginning of flowering is scaled as from "very early" to "very late". "Very early" is defined as approximately the first week of October under the prevailing conditions, while "very late" is defined as approximately the first week of December. 'Yael' is scaled as "early to medium", while 'Dorit' is between "very early to early" and "early", and 'Oso Grande' is "late to very late".

Strawberry plants have dichotome inflorescences, thus producing one primary, two secondary and four tertiary flowers per inflorescence. Flowers of higher order do not normally produce commercial fruit.

TABLE 2

FRUIT CHARACTERISTICS OF YAEL

| CHARACTERISTIC | DESCRIPTION |
|---|---|
| Time of first ripening | Early to Medium |
| Primary Fruit | |
| 1) Length | 50–56 mm |
| 2) Width | 42–55 mm |
| 3) Shape | Conical |
| 4) Weight | ca. 48 g |
| Secondary Fruit | |
| 1) Length | 48–54 mm |
| 2) Width | 40–45 mm |
| 3) Shape | Conical |
| 4) Weight | ca. 38 g |
| Tertiary Fruit | |
| 1) Length | 45–53 mm |
| 2) Width | 35–40 mm |
| 3) Shape | Conical |
| 4) Weight | ca. 25 g |
| Band without achenes | narrow |
| Unevenness of surface | Absent or very weak |
| Color | Red 45A |
| Evenness of color | Even |
| Glossiness | Medium |
| Insertion of achenes | Bellow surface |
| Insertion of calyx | In a basin |
| Pose of calyx segments | Clasping or detached |
| Size of calyx in relation to fruit diameter | larger |
| Adherence of calyx | Strong |
| Firmness | Firm |
| Color of Flesh | Orange red 43B |
| Evenness of flesh color | Slightly Uneven |
| Sweetness | Medium |
| Acidity | Medium |

The time of first ripening, approximately one month after beginning of flowering, is scaled as from "very early" to "very late". "Very early" is defined as approximately the first week of November, while "very late" is defined as approximately the first week of January. 'Yael' is scaled as "early to medium", while 'Dorit' is between "very early to early" and "early", and 'Oso Grande' (U.S. Plant Pat. No. 6,578) is "late to very late". The shape of 'Yael' fruit is similar to that of the variety 'Dorit'.

TABLE 3

COMPARATIVE YIELD OF YAEL

| | November | December | January | February | March | April |
|---|---|---|---|---|---|---|
| 'Yael' | 30 | 50 | 100 | 120 | 130 | 120 |
| 'Dorit' | 30 | 70 | 100 | 100 | 100 | 100 |
| 'Ofra' | 50 | 60 | 60 | 100 | 100 | 100 |
| 'Chandler' | 0 | 0 | 30 | 150 | 150 | 120 |

Average yield in g/m$^2$, in Ramat, Hadar, Israel. The time of beginning of ripening for 'Yael' fruit is the end of November. The time of ripening for 'Ofra' (infra short day U.S. Plant Pat. No. 8,746) fruit is "very early". The time of ripening for 'Dorit' (infra short day U.S. Plant Pat. No. 7,869) fruit is between "very early to early" and "early". The time of ripening for 'Chandler' (short day U.S. Plant Pat. No. 5,262) fruit is "very late".

TABLE 4

COMPARATIVE FRUIT CHARACTERISTICS OF YAEL

| | T.S.S.[a] | Acidity[b] | Aroma[c] | Taste |
|---|---|---|---|---|
| 'Yael' | 8.0–9.0 | 0.9 | 4 | Good |
| 'Dorit' | 8.5–9.5 | 1.0 | 5 | Good |
| 'Ofra' | 8.0–9.5 | 1.0 | 4 | Good |
| 'Chandler' | 6.5–7.5 | 0.8 | 4 | Slightly acidic |

[a]Total Soluble Solids (Sugars) expresses fruit sweetness and was determined with a refractometer for strawberry fruit a T.S.S. of 14.0 is very sweet, while below 6.5 is not sweet.

TABLE 4-continued

COMPARATIVE FRUIT CHARACTERISTICS OF YAEL

| | T.S.S.[a] | Acidity[b] | Aroma[c] | Taste |
|---|---|---|---|---|

[b]Percent of acidity was determined as follows: 2 cc of juice extract was mixed with 20 cc of water. Five drops of phenolphthalein was added and the mixture was titrated with NaOH. The percent acidity is calculated as the quantity of NaOH (cc) × 0.32.

[c]The aroma value is a subjective expression obtained by tasting, using a scale from 1 (no aroma) to 5 (strong aroma).

a. Total Soluble Solids (Sugars) expresses fruit sweetness and was determined with a refractometer; for strawberry fruit a T.S.S. of 14.0 is very sweet, while below 6.5 is not sweet.

b. Percent of acidity was determined as follows: 2 cc of juice extract was mixed with 20 cc of water. Five drops of phenolphthalein was added and the mixture was titrated with NaOH. The precent acidity is calculated as the quantity of NaOH (cc) ×0.32. The aroma value is a subjective expression obtained by tasting, using a scale from 1 (no aroma) to 5 (strong aroma).

What is claimed is:

1. A new distinct variety of strawberry plant substantially as illustrated and described and distinguished as being able to grow in September and produce fruit starting in November and lasting until summer, with fruit having a good taste and shape.

* * * * *